(12) United States Patent
Berk et al.

(10) Patent No.: US 6,474,989 B1
(45) Date of Patent: Nov. 5, 2002

(54) DENTAL MIRROR AND PROTECTIVE MASK WITH INTEGRAL REMOVAL TAB

(75) Inventors: Kenneth J. Berk, Newton; Fredrick M. Berk, Brookline; Donald Berk, Newton, all of MA (US)

(73) Assignee: Pulpdent, Watertown, MA (US)

( * ) Notice: Subject to any disclaimer, the term of this patent is extended or adjusted under 35 U.S.C. 154(b) by 0 days.

(21) Appl. No.: 09/896,330

(22) Filed: Jun. 29, 2001

(51) Int. Cl.7 .................................................. A61B 1/24
(52) U.S. Cl. ......................................................... 433/30
(58) Field of Search ............................... 433/28, 29, 30, 433/31, 32, 116; 600/247, 248; 40/630, 638

(56) References Cited

U.S. PATENT DOCUMENTS 4,032,687 A * 6/1977 Hornsby, Jr. .................. 428/1
5,551,612 A * 9/1996 Hochfeld ..................... 224/219
6,142,777 A * 11/2000 Winston et al. ............... 433/30
6,254,386 B1 * 7/2001 Ohmes ........................ 433/30
2001/0039176 A1 * 11/2001 Feely ......................... 451/538

* cited by examiner

Primary Examiner—Cary E. O'Connor
(74) Attorney, Agent, or Firm—Lee & Hollander

(57) ABSTRACT

A dental mirror instrument with a reflecting surface comprising a metallized film or other reflecting material covered by a protective mask with at least one integral removal tab. Individual mirror/mask assemblies are cut from a multi-layer laminate which includes a release layer on the bottom which is adhesively attached to a thin, reflecting film, which is in turn attached to a protective mask layer. The cutting process creates a shaped reflecting surface covered by a protective mask that is congruent with the reflecting surface except for one or more small tabs projecting beyond the reflecting surface which are part of the protective mask and by which the protective mask may be easily removed.

20 Claims, 2 Drawing Sheets

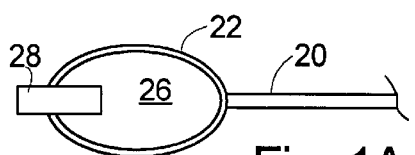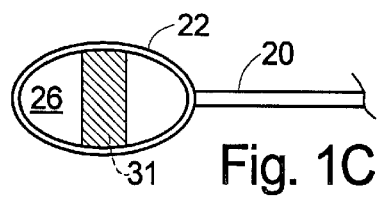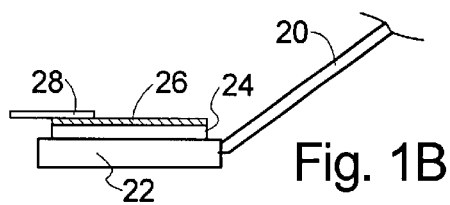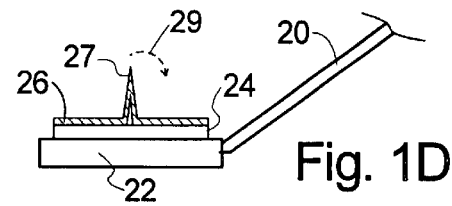
Prior Art
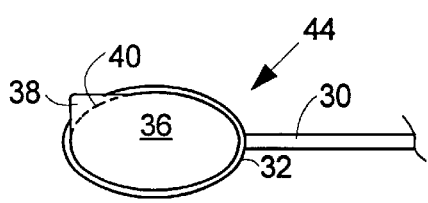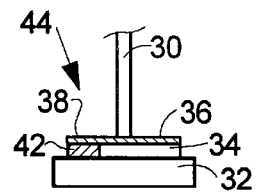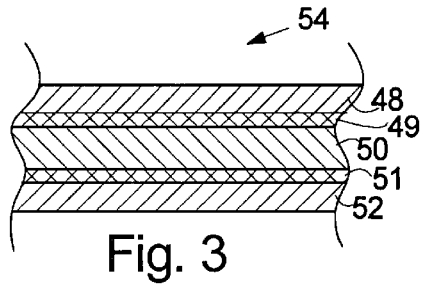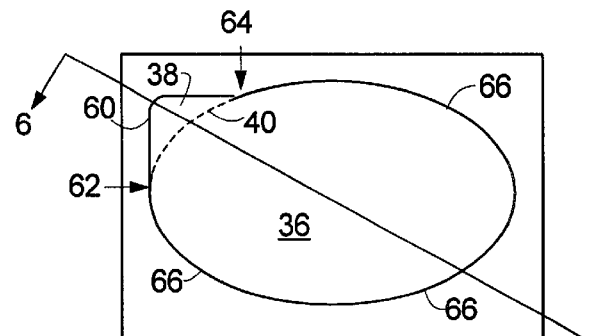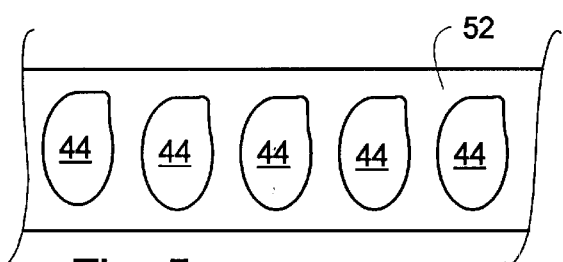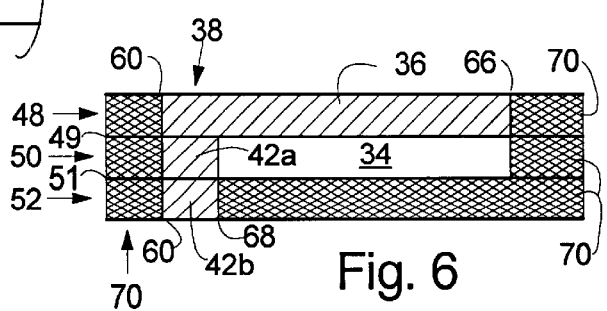

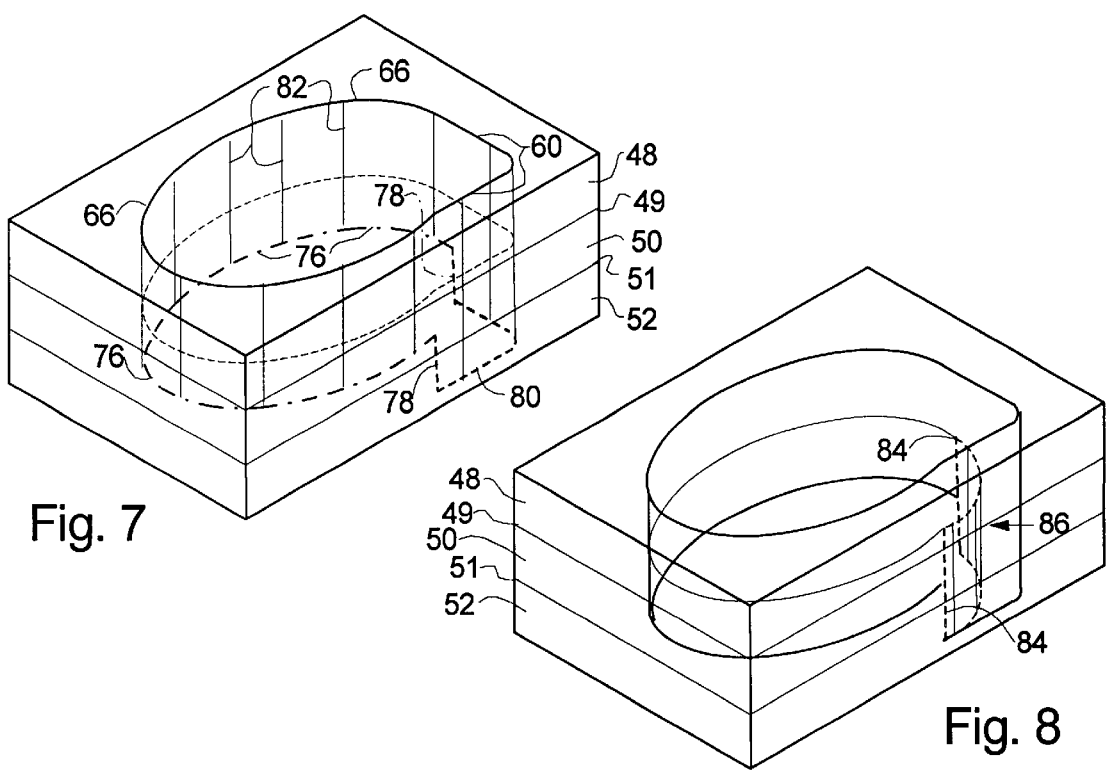

DENTAL MIRROR AND PROTECTIVE MASK WITH INTEGRAL REMOVAL TAB

FIELD OF THE INVENTION

This invention is related to small mirrors such as dental mirror instruments and particularly to a mirror with a protective mask having an integral removal tab for use with such instruments.

BACKGROUND OF THE INVENTION

Dentists have long used small, handheld mirrors when performing dental procedures such as oral surgery and restorative dentistry. The stereotypical dental mirror has a stainless handle with a reflecting surface affixed at an angle on the end of the handle. The reflecting surface in such a dental mirror is usually provided by a conventional glass mirror.

Such dental mirrors have disadvantages. They are costly to manufacture. They have a high tendency to fog up due to the relatively large heat capacity and conductance of the glass and metal materials. This type of dental mirror also requires sterilization between patients via chemical or thermal processes.

Although the material in these dental mirrors can withstand chemical and thermal sterilization, sterilizing these mirrors has several drawbacks. The interface between the glass reflective surface and the metal handle is susceptible to retaining germs which may occasionally survive the sterilization process. Even when sterilization of the mirror is successful, unsightly debris and grit may be trapped in the gap around the glass mirror and can be difficult to remove. The sterilization process is an added expense, and the glass mirror tends to develop scratches and blotches from use and sterilization.

The cost of dental mirrors becomes an important factor with a new dental technique called air abrasive dentistry. In this procedure, the dental drill normally used to remove decayed tooth material is supplemented or replaced by a high velocity air stream containing particles which abrade away the decayed tooth portions. In such procedures, an inherent problem is that some of the abrasive particles will ricochet off the tooth and impact the mirror surface with sufficient velocity to etch and damage it. Dental mirrors used in such procedures can have a very short lifetime, depending on the location of the cavity, and can become unusable within a few seconds.

For these and other reasons, disposable dental mirrors have become popular in recent years. Disposable dental mirrors may be discarded after use so sterilization is not needed and transmission of viable pathogens between patients is completely avoided. In order to be economically viable, a disposable dental mirror must be very inexpensive to manufacture and distribute. In pursuit of this goal, disposable dental mirrors have been developed that use thin, plastic, reflecting films in place of conventional rigid plastic or glass mirrors. See for example, U.S. Pat. No. 6,142,777 and U.S. patent application Ser. No. 09/633,903, assigned to the assignee of the present application.

It is important to protect the mirror surface during manufacturing and shipping. This is especially true for disposable mirrors, which are frequently packaged with a number of mirrors loaded loosely into a box or other container, and also for mirrors which have a reflecting surface made of a metallized, plastic film, whose surface is more delicate than that of glass mirrors.

One well-known method of providing protection is to apply a protective layer or mask of plastic, foil, or other material over the mirror surface. This mask is then removed by a dentist prior to use. However, this also requires provision of some method of quickly and easily removing the mask.

While masks can be removed without the provision of a removing means, this can be awkward and difficult to do. The difficulty is increased if a dentist is wearing protective gloves. Additionally, with thin film reflective surfaces, there is an increased chance of damaging the surface if no means for removing the mask is supplied.

One common mechanism for removing a mask is the provision of a separate tab attached to the top of the mask and which is used to remove the mask. Disadvantages of this method include the cost of extra steps required to attach the tab, a tendency to attract debris by the adhesive used to attach the tab, and the fact that it is not uncommon for a small percentage of such tabs to come loose and fail.

Another method for providing a means for removal is to fold the mask back on itself so that a piece of the mask material protrudes from the surface of the mirror where it can be grasped. While this method reduces the problems of failed tabs and or debris sticking to the tab, it requires more expensive machinery to carry out.

SUMMARY OF THE INVENTION

The present invention includes a new system for providing a dental mirror with a reflecting surface comprising a metallized film or other reflecting material covered by a protective mask with an integral removal tab that may be quickly and easily applied to a dental mirror handle and mirror substrate by automatic machinery.

In this system, mirror assemblies are cut from a multi-layer laminate which includes a release layer on the bottom which is adhesively attached to a thin, reflecting film, which is in turn attached to a protective mask layer. Individual mirror/mask assemblies are die cut from the multi-layer assembly by a cutting process that creates a shaped reflecting surface covered by a protective mask that is congruent with the reflecting surface except for the addition of one or more small tabs projecting beyond the reflecting surface which are part of the protective mask and by which the protective mask may be easily removed.

DESCRIPTION OF THE DRAWINGS

The advantages and operation of the present invention are more fully set forth in the following description of the preferred embodiment and by reference to the drawings, of which:

FIGS. 1A through 1D show prior art removal tabs;

FIGS. 2A and 2B are top and front views respectively of a dental mirror having a protective mask with an integral tab in accordance with the present invention;

FIG. 3 shows a multi-layer lamination that may be used to make the mirror and mask shown in FIGS. 2;

FIG. 4 is a top view showing cuts made in the laminate of FIG. 3 to create mirror/mask assemblies;

FIG. 5 illustrates how multiple mirror/mask assemblies may be formed on a roll of laminate for automatic placement on a dental mirror instrument head;

FIG. 6 is a sectional view along the section line indicated in FIG. 4 illustrating the cuts made through the various layers of the lamination of FIG. 3 in forming the mirror/mask assembly; and FIGS. 7 and 8 show first and second cutting steps for one preferred method of creating the mirror/mask assemblies of the present invention.

DESCRIPTION OF THE PREFERRED EMBODIMENT

It should be understood that the term "dental mirror instrument" as used herein will be used to refer to the entire instrument assembly, including without limitation handle, mirror head on which a reflecting surface is mounted, reflective surface, and protective mask. The term "mirror" will be used to refer to the reflecting surface of the dental mirror instrument.

FIGS. 1A and 1B are top and side views respectively illustrating a prior art method in which a separate removal tab is provided for removing a protective mask on a dental mirror instrument or similar small mirror. In FIGS. 1A and 1B, the distal portion of a dental mirror instrument is shown, including a handle section 20 connected to a head or substrate 22 on which the mirror 24 is mounted. Typically head 22 and mirror 24 are round or oval.

The top surface of mirror 24 has applied thereto a protective layer 26 which forms a mask to prevent damage to the mirror surface. Mask 26 may be made of foil or plastic, although other materials are sometimes used. An adhesive material may be used to attach the mask to mirror 24 or the mask may be made of a vinyl or other cling material that adheres to the mirror without an adhesive. The mask is designed to be removed before the mirror instrument is used, and the removal means is a tab 28 which is adhesively attached to the protective mask and which may be grasped to aid in removal.

In practice, getting this system to work requires considerable attention to details. The adhesive holding the protective mask to the mirror must have a relatively low adhesion so that the mask comes off easily and without leaving any adhesive behind on the mirror surface. The interface between the tab and the mask is much smaller in area compared to the mirror surface and is subject to significantly more force per area when the mask is pulled off. Thus, this adhesive is typically a different material requiring another machine and manufacturing step to apply. The adhesive must be applied to the tab precisely. If the adhesive spreads beyond the edge of the tab, it will tend to attract and hold debris. While this system of using a separate tab 28 to remove the protective layer is certainly achievable, it requires precision, relatively expensive equipment and has more steps than the present invention, as will become clear from the description below.

FIGS. 1C and 1D show an alternate prior art method of providing a mask removal tab. In this method, the mask layer is folded to provide an upwardly projecting removal tab 27, as shown in FIG. 1D. Before final packaging, this fold is folded downwardly, as shown by arrow 29 in FIG. 1D, so that it lies flat over the surface of the mirror in the position shown as 31 in FIG. 1C. While this method provides an integral mask tab that does not detach and also has less of a tendency to develop errant areas of adhesive that collect debris than the separate tab described above, the folded mask tab is expensive to manufacture and requires more steps than the present invention.

FIGS. 2 through 8 are illustrative of the preferred embodiment for the present invention. It should be appreciated that the figures are not drawn to scale, but rather are drawn to aid the following description which points out the distinguishing features of the invention. FIGS. 2A and 2B are top and front views of a dental mirror instrument constructed in accordance with the present invention. In FIGS. 2A and 2B, a handle portion 30 connects to the head 32 of the dental mirror instrument which provides a substrate on which the mirror 34 is mounted. In the present invention, the mirror is implemented by a thin, flexible reflective film. Typically, this is a metallized, plastic film, but the present invention may include other thin, flexible, reflective materials, such as that shown in U.S. Pat. No. 3,711,176, however made now or in the future, as will become clear from the following description.

Mask 36 has an integral tab or projection 38 that extends beyond the periphery of mirror 34 shown by dotted line 40 in FIG. 2A. The tab is grasped by a dentist to remove protective mask 36 before the dental mirror instrument is used. Tab 38 has on its underside a small section 42 of the reflecting film and a release liner, as described more fully below. Although shown as a distally projecting corner in FIGS. 2A and 2B, other shapes and locations may be selected for tab 38. The entire mask and mirror assembly 44 includes mirror 34 and mask 36 with tab portion 38 and can be applied to instrument head section 32 in a single operation.

FIG. 3 illustrates the multi-layer laminate 54 which is used to make the mirror assembly 44. Laminate 54 includes a top mask layer 48 which forms the protective mask 36 and the top surface of tab 38. This layer may be made of a thin plastic film and is preferably between 0.5 and 2 mils thick. Mask layer 48 is attached to a reflective film layer 50 by an adhesive layer 49. The adhesive material of layer 49 may be formulated of a pressure sensitive adhesive. Alternatively, mask layer may be a static cling material made of vinyl or other material that adheres to the mirror surface by means of a static charge. In this case, adhesive layer 49 would be omitted from laminate 54.

In the described embodiment, reflective film layer 50 is made of metallized plastic film, approximately 4 mils thick. Other materials which provide a thin, flexible, reflective film, preferably between 1 to 10 mils thick, may be used, as discussed above. Preferably, the metallized side of the reflective layer faces the mirror instrument head 32 so that the plastic film will provide protection for the more delicate metallization while in use. Due to the thinness of the plastic film, diffraction effects from the back-surface orientation of this mirror are negligible, and the mirror will effectively function as a front surface mirror.

The other side of layer 50 is attached to a release liner layer 52 by a second adhesive layer 51. The material of release liner 52 and the adhesive between layers 50 and 52 are chosen so that the adhesive has a very low adherence to the release liner material but has a very high adherence to both the plastic film 50 and the material from which mirror head 32 is made. In the described embodiment, the adhesive in layer 51 is a pressure sensitive adhesive and is about 1 mil thick. Release liner layer 52 may be made of plastic film and is approximately 1 mil thick. The technology of this process is well known in the labeling and related fields, and suitable materials other than the materials set forth above may be readily substituted by one of ordinary skill in the art in implementing the present invention.

In FIGS. 4–8, the thickness of the adhesive layers is minimized so that the drawings may more clearly show the cuts that are made through the mask, reflecting, and release liner layers.

In order to make each of the mirror assemblies 44, a series of cuts must be made. Referring to FIGS. 3 and 4, a cut through all three layers 48, 50, and 52 must be made along the periphery 60 of tab 38 between the points denoted by arrows 62 and 64. A second cut must be made through mask layer 48 and reflective film layer 50 along line 66 which defines the periphery of mirror 34 between points 62 and 64. This forms the entire edge of the mirror, except where the edge, denoted by dotted line 40, lies adjacent to tab 38 along the border between the mirror and the tab. A third cut is made from the bottom of the release liner along dotted line 40. This cut goes through the release liner layer 52 and the reflecting film layer 50 leaving mask layer 48 intact over the mirror 36 and the tab area 38. It should be noted that these cuts may be made in various combinations so that three, separate cutting steps are not usually required.

Typically, a large number of mirror assemblies 44, such as shown in FIG. 5, are formed in a long ribbon suitable for use with known types of automatic label application machinery. A single roll may contain ten to fifteen thousand or more individual mirror assemblies. This ribbon would then be loaded into the application machinery, which will take individual mirror assemblies and automatically apply them to the heads of individual dental mirror instruments. Although this is a preferred embodiment, the present invention may also be used to make individual mask and mirror assemblies or mask and mirror assemblies formed in arrays or other patterns.

Tab 38 may be made in many other configurations than that shown and described, including projections that extend from the ends or the sides of the mirror assembly. The present invention may also be used to form a mask and mirror assembly with multiple tabs, any of which may be used to remove the protective mask. For example, two tabs similar to that shown in FIGS. 2A and 2B could be provided, one on each side of the mirror head, to allow easy removal by either hand. Another embodiment of the invention is to provide a continuous tab area that surrounds the reflective surface so that the protective mask may be grasped at any point along its circumference for removal.

Since the preferred shape for dental mirrors is round or oval, however, tabs formed as a corner protrusion minimize the amount of wasted material. In actual practice, the space between individual mirror assemblies and the borders along the edges of the ribbon would be much smaller than shown in FIG. 5, resulting in very little wasted material and thus lower costs.

FIG. 6 is a sectional view through the laminate taken at line 6—6 in FIG. 4 which more fully shows the configuration produced by the above-described method. In FIG. 6, cut 60 goes through all three layers of the laminate and defines the periphery of tab 38. Cut 66 goes through the mask and reflective film layers 48 and 50 and defines the periphery of the final mirror except where it lies adjacent to tab 38. Cut 68 goes through the release liner and reflective film layers 52 and 50 to form the mirror edge 40 under tab 38.

When these cuts are made, a labeling machine can apply as an integral assembly the segment of reflecting film 34 that will form the mirror, along with the areas marked with diagonal hatching in FIG. 6, which include protective mask 36, and segments 42*a* and 42*b*, which are pieces of the reflecting film and the release liner respectively which lie under removal tab 38. This assembly is placed on the head 32 of the dental instrument, as shown in FIGS. 2A and 2B. Segments 42*a* and 42*b* remain after placement of the mirror and serve to prevent the adhesives in layers 49 and 51 under tab 38 from sticking to the plastic base or attracting debris. They are removed as part of the tab when a dentist takes off the protective mask 36. The cross hatched areas marked 70 in FIG. 6 are waste. Typically, the waste pieces 70 in layers 48 and 50 are stripped off during the die cutting process leaving individual mirror assemblies 44 on a substrate of release liner 52, as shown in FIG. 5. The release liner 52, except for protective piece 42*b*, is removed during the application of the mirror assemblies to the mirror heads 32.

When a dentist is ready to use the mirror instrument, he or she will grasp tab 38 and remove the protective mask 36, along with all the diagonally hatched segments shown in FIG. 6 leaving the portion of reflective layer 50 that forms mirror 34 attached to the mirror head.

While the cuts shown in FIGS. 4 and 6 and described above may be made in different ways, FIGS. 7 and 8 illustrate a two-stage process that is preferred. In FIG. 7, a two-step die is used to make an initial, two-level cut. The first level extends through the top two layers 48 and 50 ending in the curved boundary denoted by dot-dash line 76. The die then steps down as denoted by vertical dashed lines 78 to form a second level of cut that goes through all three layers. This cut forms the tab periphery and extends to the bottom of the release liner layer, as denoted by dashed line 80 in FIG. 7. The walls of the resulting cut, as well as the shape of the cutter, are illustrated by vertical lines 82 in FIG. 7.

A second cut is made from the other side of the laminate, as shown in FIG. 8. This cut extends upward through the release liner and the reflective film and follows the periphery of the mirror under the tab, as shown by dashed lines 84 and vertical lines 86. This cut corresponds to cut 68 shown in FIG. 6 and completes the mirror peripheral cut through the reflective film.

An alternate method for forming mirror assemblies 44 is to first cut through the top two layers along the periphery of the protective mask. This would be the equivalent of making the cut shown in FIG. 7 with a single level die that does not have step 80 that cuts the release liner. A second cut is made with a two-step die that cuts only the release liner 52 along the outer border of the tab and cuts the release liner 52 and the reflective film 50 along line 40 that defines the border between the mirror and the tab. This method is less preferred than the method described above, since the alignment of the second or bottom die is easier to control when the die is cutting only a single line.

In the embodiment described above, segments 42*a* and 42*b* under the removal tab serve to prevent the adhesive under the tab from attracting debris. This method is very practical because it inexpensive, requiring no additional materials or manufacturing steps. In another embodiment of the present invention, the mirror assembly could be formed so as to leave segments 42*a* and 42*b* behind as waste with the removal tab being a unitary layer.

In this embodiment, the adhesive in layer 49 might then be neutralized by means of a solvent, being covered by a powder, or otherwise. Alternatively, the adhesive, which has a low coefficient of adhesion to allow it to be easily removed from the mirror surface, might be left alone. This embodiment is especially suitable if the protective mask 38 is formed from a static cling vinyl material or the like, since then there is no adhesive that needs to be covered.

To form such an assembly with a process such as that shown in FIGS. 7 and 8, for example, the cut of FIG. 7 would have a step up in place of the step down shown by lines 78 and 80 so that the first cut only extends through the mask layer 48 along the periphery of tab 38. The second cut shown in FIG. 8 would be the same. This process results in the release liner and reflective film under the tab remaining attached to the rest of the laminate after the two-step cutting operation. Other methods of performing this operation will be obvious to those skilled in the art.

In yet another embodiment of the invention, film segment 42a remains attached to the underside of tab 38 with the release liner segment 42b being discarded as waste. One method of doing this would be to modify the FIG. 7 cut so that it is a single-level cut going through the top two layers. The FIG. 8 cut would remain the same. This method is less preferred than those described above, however, due to the much higher coefficient of adhesion typical of adhesive layer 51.

There has been described a new and useful configuration for a dental mirror and protective mask with an integral removal tab along with a method for manufacturing it. While the operation and advantages of the invention have been explained with reference to the exemplary embodiments described above, it should be appreciated that modifications to these embodiments will be made by those of ordinary skill in the art in applying the teachings of the invention to different situations and applications. Accordingly, the present invention should not be limited by the embodiments described above, but rather the scope of the invention should be interpreted in accordance with the following claims.

What is claimed is:

1. A method of manufacturing a dental mirror instrument having a handle and a head and including a mirror covered by a one-piece protective mask with a removal tab section that includes at least one integral removal tab which extends beyond the periphery of the mirror, the method comprising the steps of:

providing a laminate including at least a mask layer overlying an intermediate reflective film layer and a release liner layer;

making a cut through at least the mask layer along the periphery of the removal tab section;

making a cut through the mask layer and the reflective film layer along a line that follows the periphery of the mirror except along the border between the mirror and the removal tab section where the mirror lies adjacent to the removal tab section;

making a cut through the release liner layer and the reflective film layer along the border between the removal tab section and the mirror; and removing the mirror and protective mask from the release liner and attaching the reflective film to the mirror instrument head.

2. The method of claim 1 further including the step of attaching the release liner layer to the reflective film layer by means of an adhesive.

3. The method of claim 2 further including the step of attaching the mask layer to the reflective film layer by means of a second adhesive.

4. The method of claim 3 further including the step of providing a means for covering the second adhesive in the area underneath the removal tab section.

5. The method of claim 4 further including the steps of:

making a cut through the reflective film layer and the release liner layer along the periphery of the removal tab section; and leaving sections of the release liner layer and the reflective film layer attached to the underside of the removal tab section to provide the means for covering the second adhesive.

6. The method of claim 5 wherein the cuts are made via a process including the steps of:

making a cut with a two-step die from the mask side of the laminate which cuts through the mask layer and the reflective film layer along the mirror periphery where it is not adjacent to the removal tab section and which cuts all the way through the laminate along the periphery of the removal tab section; and making a cut from the release liner layer side of the laminate that cuts through the release liner layer and the reflective film layer along the border between the mirror and the removal tab section.

7. The method of claim 2 wherein the mask layer is made of a static cling material and further including the step of removing the release liner and the reflective film layers from underneath the removal tab section.

8. The method of claim 1 including the steps of:

repeatedly performing the cutting steps at different positions on the laminate to create a plurality of mirror assemblies, each including a reflective film mirror covered by a protective mask with an integral removal tab section; and sequentially applying individual mirror assemblies to separate mirror instrument heads.

9. The method of claim 1 further including the steps of:

making a cut through the reflective film layer and the release liner layer along the periphery of the removal tab section; and leaving sections of the release liner layer and reflective layer attached to the underside of the removal tab section.

10. The method of claim 1 wherein the cuts are made via a process including the steps of:

making a first cut from the mask layer side of the laminate with a two-step die which cuts through the reflective film layer and the mask layer along the mirror periphery where it is not adjacent to the tab section and which cuts all the way through the laminate along the border of the removal tab section;

making a second cut from the release liner layer side of the laminate that cuts through the release liner layer and the reflective film layer along the border between the mirror and the removal tab section; and where the step of removing includes the step of leaving pieces of reflective film and release liner attached to the underside of the removal tab section.

11. The method of claim 1 further including the step of providing a continuous removal tab that extends beyond the periphery of the mirror along its entire circumference, wherein said first-stated cut-making step includes making a cut through at least the mask layer that extends beyond the periphery of the mirror along its entire circumference to form a single, integral, circumferential removal tab that extends around the mirror periphery; and wherein said third-stated cut-making step includes making a cut through the release liner layer and reflective film layer along the border between the mirror and the circumferential removal tab.

12. The method of claim 1 further including the step of providing multiple removal tabs, wherein said first-stated cut-making step includes making a plurality of cuts through at least the mask layer that extend beyond the periphery of the mirror in a plurality of separated locations along the periphery of the mirror to form a plurality of integral removal tabs in the protective mask; and wherein said third-stated cut-making step includes making a plurality of cuts through the release liner layer and reflective film layer along the borders between the mirror and the plurality of removal tabs.

13. A method of manufacturing a dental mirror instrument having a mirror covered by a protective mask having a removal tab section that includes at least one integral removal tab which extends beyond the periphery of the mirror, comprising the steps of:

providing a dental mirror instrument assembly including a handle attached to a head section adapted to carry a reflecting mirror;

providing a 3-layer laminate including: a middle layer made of a thin reflecting film;

a mask layer on the top surface of the film layer for providing protection to the reflecting film attached to the film layer by a means for attaching that allows for relatively easy removal of the mask layer from the reflective film; and a release liner on the bottom surface of the reflecting film attached to the film layer by an adhesive that releases easily from the release liner while adhering strongly to the reflective film and the material from which the head section is made;

creating a mirror assembly in the laminate by:
making a cut through the mask and film layers, the cut being made along a line that follows the mask periphery including the removal tab section;
making a cut through the release liner layer along the periphery of the removal tab section;
making a cut through the release liner layer and the film layer which follows the periphery of the removal tab section, and which connects with the edges of the first cut in the film layer; and removing the mirror assembly, including the mirror and protective mask, from the release liner and applying it to said head section.

14. The method of claim 13 wherein the means for attaching includes an adhesive material.

15. A dental mirror, comprising:

a handle section adapted for being manually held;

a head section attached to the handle section and having a flat, planar surface to which a mirror can be attached;

a mirror comprising a thin, flexible, reflective film adhesively attached to said flat surface; and a manually-removable protective mask made of a single piece of a thin, flexible material covering the mirror surface, and including one or more integral removal tabs that extend beyond the mirror periphery;

wherein the protective mask is attached to the mirror surface with a second adhesive spread over the bottom surface thereof and further comprising means for covering the adhesive in the areas of the removal tab.

16. The mirror of claim 15 wherein the boundary of the head section is rounded or oval in shape and wherein the integral removal tab includes a triangular shaped portion extending beyond the boundary of the head.

17. The mirror of claim 15 wherein the reflective film comprises a plastic film metallized on one side.

18. The mirror of claim 15 wherein the means for covering the adhesive includes at least a piece of reflective film covering the second adhesive in the area of the removal tab.

19. A method of manufacturing an array of dental mirror assemblies suitable for application to a dental mirror instrument head section by automatic machinery, each assembly including a mirror covered by a protective mask having at least one integral removal tab which extends beyond the periphery of the mirror, comprising the steps of:

providing a 3-layer laminate including:
a middle layer made of a thin reflecting film;
a mask layer on the top surface of the film layer for providing protection to the reflecting film attached to the film layer by a means for attaching that allows for relatively easy removal of the mask layer from the reflective film; and
a release liner on the bottom surface of the reflecting film attached to the film layer by an adhesive that releases easily from the release liner while adhering strongly to the reflective film and the material from which the head section is made;

creating a plurality of mirror assemblies in the laminate by repeatedly:
making a cut through the mask and film layers, the cut being made along a line that follows the mask periphery of each mirror assembly including the removal tab;
making a cut through the release liner layer along the periphery of the removal tab section of each mask assembly; and
making a cut through the release liner layer and the film layer which follows the periphery of the removal tab section, and which connects with the edges of the first cut in the film layer of each mask assembly.

20. The method of claim 19 wherein the means for attaching includes an adhesive material.

* * * * *